(12) United States Patent
Jeng

(10) Patent No.: US 10,981,787 B2
(45) Date of Patent: Apr. 20, 2021

(54) OXYGEN GENERATOR

(71) Applicant: CoolerBIT Technology Ltd., Taoyuan (TW)

(72) Inventor: Jian-Dih Jeng, Taoyuan (TW)

(73) Assignee: COOLERBIT TECHNOLOGY LTD, Taoyuan (TW)

( * ) Notice: Subject to any disclaimer, the term of this patent is extended or adjusted under 35 U.S.C. 154(b) by 549 days.

(21) Appl. No.: 15/960,689

(22) Filed: Apr. 24, 2018

(65) Prior Publication Data

US 2019/0002280 A1    Jan. 3, 2019

(30) Foreign Application Priority Data

Jun. 30, 2017  (TW) ................................ 106209681

(51) Int. Cl.
| | |
|---|---|
| *A61L 9/00* | (2006.01) |
| *A61M 15/00* | (2006.01) |
| *B65D 25/08* | (2006.01) |
| *C01B 13/02* | (2006.01) |
| *A62B 21/00* | (2006.01) |
| *A61M 16/10* | (2006.01) |
| *B01J 19/24* | (2006.01) |

(52) U.S. Cl.
CPC ..... *C01B 13/0211* (2013.01); *A61M 16/1005* (2014.02); *A62B 21/00* (2013.01); *B01J 19/24* (2013.01); *B01J 2208/00814* (2013.01); *B01J 2219/00162* (2013.01); *B01J 2219/24* (2013.01); *B01J 2219/30207* (2013.01)

(58) Field of Classification Search
CPC ...... C01B 13/0211; B01J 19/24; A62B 21/00; A61M 16/1005
USPC ......... 422/305; 128/200.24, 202.26; 206/219
See application file for complete search history.

(56) References Cited

U.S. PATENT DOCUMENTS 6,267,114 B1 * 7/2001 Ueno ..................... A62B 21/00
                                                       128/200.24

* cited by examiner

*Primary Examiner* — Monzer R Chorbaji
(74) *Attorney, Agent, or Firm* — McClure, Qualey & Rodack, LLP

(57) ABSTRACT

An oxygen generator includes a bag body and supporting components. The bag body is configured to contain a reactive liquid, a reactant and a catalyst, and the bag body includes a bag piece, a circumferential sealing part and separation parts. The circumferential sealing part is bound with a part of the periphery of the bag piece, so as to define a range of an inner space, and a range of the rest part of the periphery of the bag piece defines an opening. Both ends of each separation part are connected to the circumferential sealing part so as to separate the inner space into a plurality of separate spaces, and the plurality of separate spaces respectively contain the reactant and the catalyst. The supporting components are contained in one of the plurality of separate spaces, and the positions, corresponding to the supporting components, of the bag body are incompressible.

17 Claims, 8 Drawing Sheets

OXYGEN GENERATOR

CROSS-REFERENCE TO RELATED APPLICATION

This non-provisional application claims priority under 35 U.S.C. § 119(a) to Patent Application No. 106209681 filed in Taiwan, R.O.C. on Jun. 30, 2017, the entire contents of which are hereby incorporated by reference.

BACKGROUND

Technical Field

The present invention relates to a preparation device related to chemistry, and particularly relates to an oxygen generator.

Related Art

Oxygen is one of important elements for sustaining human lives and energies, and therefore, there is obviously no need to say the demands of the human body on oxygen. A sufficient oxygen supply is beneficial to relieving fatigue and clearing the head. Besides maintaining the normal operation of somatic functions, oxygen can be used for medical treatment and emergency treatment (for example, emergency treatment on patients with asthma), or can avoid the loss of life and property in case of a fire accident if a carry-on oxygen generator can be used.

There are several types of existing oxygen generators as follows: (1) a pressure-type oxygen steel cylinder: oxygen is filled into a steel cylinder under high pressure by a compressor and is stored in the steel cylinder, and is supplied to a user in combination with a respirator when oxygen is needed; (2) an air-separation-type oxygen generator: a molecular sieve is utilized to filter compressed air, so as to separate out oxygen; and (3) a chemical-reaction-type oxygen generator: a catalyst is utilized to perform a chemical action on an oxygen-generating agent in the device, so as to accelerate the decomposition of oxygen molecules in the oxygen-generating agent and supply oxygen.

However, the foregoing oxygen generators have their respective defects. The oxygen steel cylinder has the defects of large volume and difficulty in storage, and the oxygen must be supplemented at a specific location; and in addition, the compressor has to use a power supply to pressurize the oxygen, so the overall device is complex. The air-separation-type device is expensive, and also has to use a power supply to filter air; the air-separation-type device has a large volume, and thus, can only be arranged at a specific place; and the air-separation-type device needs periodical maintenance. The chemical-reaction-type device needs a heat source to have a decomposition effect if sodium perborate is used as the oxygen-generating agent.

In conclusion, the biggest defect of the existing oxygen generators is the difficulty in carrying about; and in case of an emergency demanding oxygen for medical treatment, the existing oxygen generators cannot immediately supply oxygen. In addition, as for the chemical-reaction-type device, the oxygen-generating agent must be manually supplemented after the oxygen-generating agent stops generating oxygen; however, the oxygen-generating agent is not be easily carried about and stored.

SUMMARY

The present invention provides an oxygen generator, and mainly aims to provide a carry-on oxygen generator.

In order to achieve the above-mentioned goal, the present invention provides an oxygen generator, which includes a bag body and supporting components. The bag body is configured to contain an oxygen-generating agent, the oxygen-generating agent includes reactive liquid, a reactant and a catalyst, and the bag body includes a bag piece, a circumferential sealing part and separation parts. The bag piece is provided with a periphery. The circumferential sealing part is arranged on a part of the periphery of the bag piece and is bound with the periphery of the bag piece, the circumferential sealing part enables the binding of part of the periphery so as to define a range of an inner space, and a range of the rest part of the periphery of the bag piece defines an opening. Each separation part is provided with a breakthrough part, both ends of each separation part are connected to the circumferential sealing part so as to separate the inner space into a plurality of separate spaces, and the plurality of separate spaces respectively contain the reactant and the catalyst. The supporting components are contained in one of the plurality of separate spaces, and the positions, corresponding to the supporting components, of the bag body are incompressible.

Thereby, all substances of the oxygen-generating agent are separately packed in different separate spaces in the soft bag body, and the separate spaces in the bag body communicates with one other by pressing the bag body, so that the substances of the oxygen-generating agent are mixed and react to generate oxygen. Compared with an oxygen generator with an oxygen-generating agent contained in incompressible containers, the oxygen generator of the present invention can obviously reduce the volume occupation, is very convenient to use, and is more convenient to carry about.

DETAILED DESCRIPTION

Figure 1:
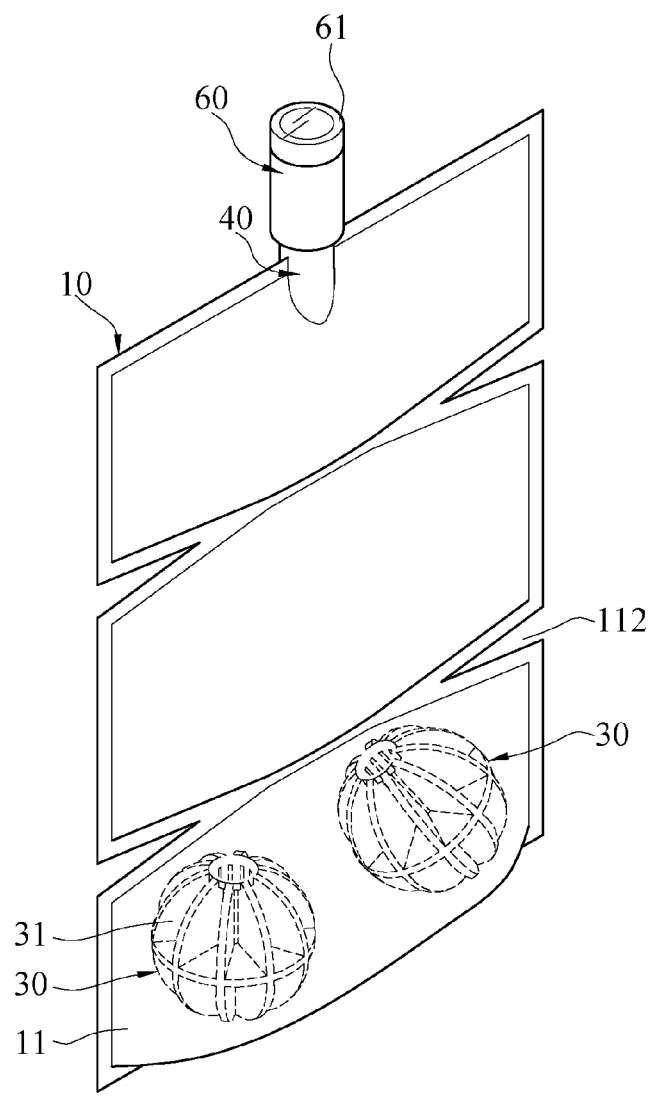
FIG. 1 is an appearance schematic diagram of a three-dimensional structure of an embodiment of an oxygen generator of the present invention.
Figure 2:
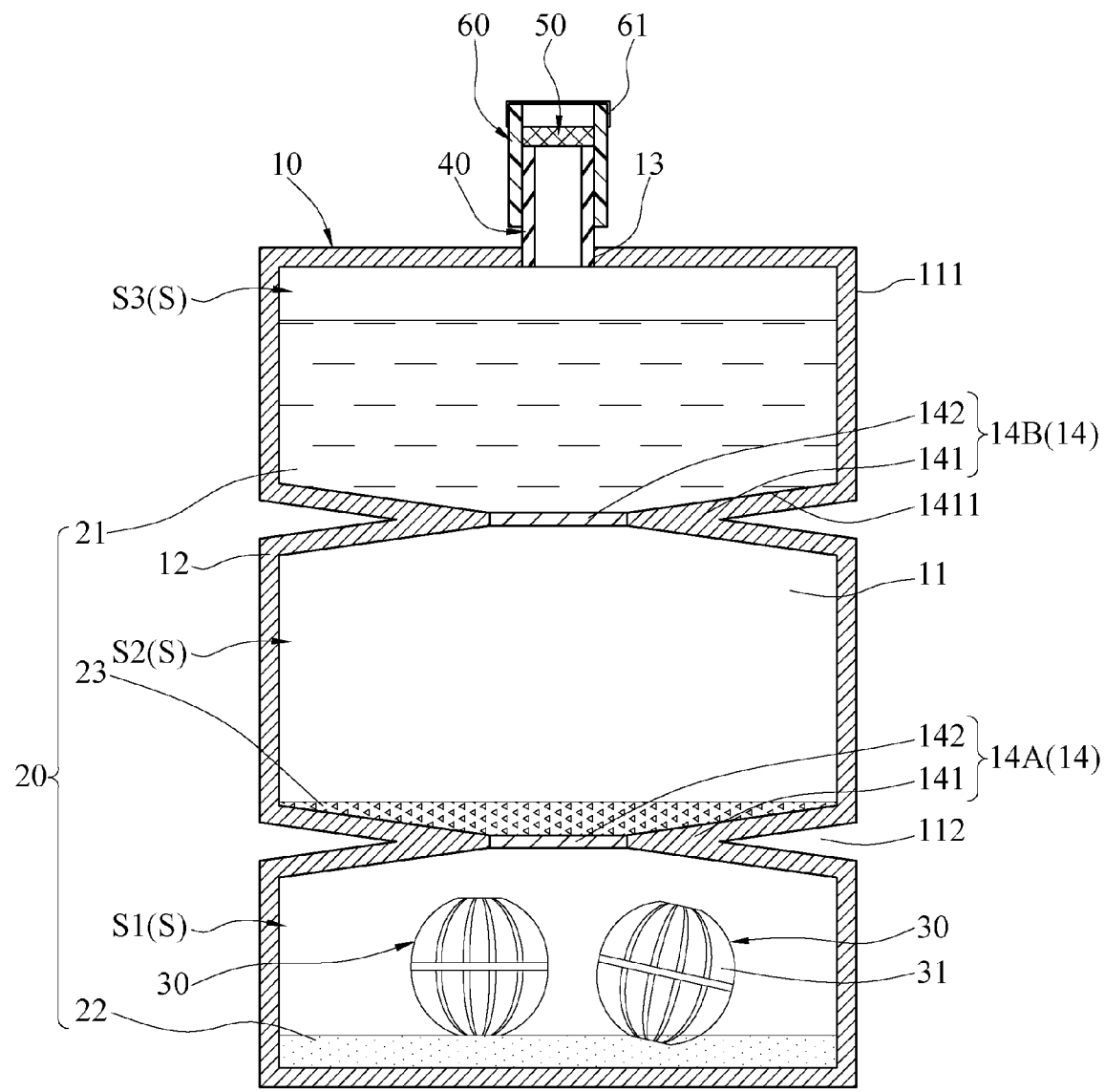
FIG. 2 is a section view of a local structure of an embodiment of the oxygen generator of the present invention.

Referring to FIG. 1 and FIG. 2, FIG. 1 is an appearance schematic diagram of a three-dimensional structure of an embodiment of an oxygen generator of the present invention; and FIG. 2 is a section view of a local structure of an embodiment of the oxygen generator of the present invention.

Referring to FIG. 2, the oxygen generator includes a bag body 10 and supporting components 30. The bag body 10 is configured to contain an oxygen-generating agent 20 including reactive liquid 21, a reactant 22 and a catalyst 23, and the supporting components 30 are contained in the bag body 10. A periphery 111 of the bag body defines an inner space and an opening 13 by using a circumferential sealing part 12, and the inner space of the bag body 10 is separated into a plurality of separate spaces S through separation parts 14. The plurality of separate spaces S respectively contains the reactant 22 and the catalyst 23. The bag body 10 can be filled with the reactive liquid 21 before use or in advance, so as to perform chemical reaction with the reactant 22 in the bag body 10 under the action of the catalyst 23 and generate oxygen. The supporting components 30 are contained in one of the plurality of separate spaces S, so that the positions, corresponding to the supporting components 30, of the bag body 10 are incompressible. When a force is applied to the bag body 10 to separate a breakthrough part 142, between every two separate spaces S, of the separation part 14, the separate spaces S communicate, so that the reactive liquid 21, the reactant 22 and the catalyst 23 can be mixed and act to generate oxygen.

Referring to FIG. 2, in an embodiment, the bag body 10 includes a bag piece 11, a circumferential sealing part 12, an opening 13 and separation parts 14. The bag piece 11 seals a part of the periphery 111 through the circumferential sealing part 12 and defines a range of the inner space and an opening 13, and the separation parts 14 separate an inner space of the bag body 10 into a plurality of separate spaces S.

Further referring to FIG. 2, the bag piece 11 is provided with the periphery 111, and a surrounding range of the periphery 111 of the bag piece 11 defines a range of the inner space of the bag body 10. The bag piece 11 can be a single bag piece 11 or a plurality of bag pieces 11 are included. The single bag piece 11 can be bent so that the periphery 111 is connected and forms a circle to define a range of the inner space. The plurality of bag pieces 11 can be spliced so that the peripheries 111 of the plurality of bag pieces 11 are connected and form a circle to define the range of the inner space.

Referring to FIG. 2, the circumferential sealing part 12 is arranged on a range of part of the periphery 111 of the bag piece 11, the circumferential sealing part 12 enables the binding of the part of the periphery 111 to define the range of the inner space, and a range of the rest part of the periphery 111 of the bag piece 11 is distinguished and defines an opening 13, so that the opening 13 communicates with the inner space of the bag body 10. In an embodiment, the circumferential sealing part is formed by hot sealing.

Also referring to FIG. 2, the separation parts 14 separate the inner space of the bag body 10 into the separate spaces S by binding two parts of the bag piece 11 or binding two bag pieces 11. Each separation part 14 includes a separate sealing part 141 and a breakthrough part 142, and both ends of each separation part 14 are connected to the circumferential sealing part 12, so that the separate spaces S is defined between the separation parts 14 and the circumferential sealing part 12. In an embodiment, each separation part 14 includes two separate sealing parts 141 and a breakthrough part 142, the breakthrough part 142 is positioned between the two separate sealing parts 141, and the separation part 14 is connected to the circumferential sealing part 12 through the two separate sealing parts 141. Certainly, each separation part 14 can only include a single separate sealing part 141 and a single breakthrough part 142, and thus, the separation part 14 can be connected to the circumferential sealing part 12 through the separate sealing part 141 and the breakthrough part 142.

The separate sealing part 141 is of an inseparable binding structure, and the breakthrough part 142 is of a separable binding structure. In an embodiment, the breakthrough part 142 is separated when receiving a tensile force, but is not limited to this. In other words, the breakthrough part 142 can be separated under pressure or can be separated in combination with other binding structures. The separation of the breakthrough part 142 is not the separation that the bag body 10 becomes an open state, but the phenomenon that the breakthrough part 142 is separated in the bag body 10 so that the separate spaces S communicate with each other.

In an embodiment, when a direction of the foregoing tensile force or a direction of a force component thereof conforms to a projection direction of the surface of the bag piece 11, the breakthrough part 142 can be separated. Thereby, the separate sealing part 141 is of a sealed-for-life binding structure formed by hot sealing, and the breakthrough part 142 is of a temporary binding structure formed by hot sealing.

In other embodiments, the breakthrough part 142 can be a zipper lock. Thereby, in order to facilitate the separation of the breakthrough part 142, a position, corresponding to the breakthrough part 142, outside the bag body 10 can be provided with a pull part by which a user can apply a force and pull, and the user enables the zipper lock to be separated by applying a force to the pull part, so that the oxygen-generating agent 20 can be thoroughly mixed and further perform an oxygen-generating reaction.

In addition, when a plurality of separation parts 14 are arranged in the bag body 10, one separation parts 14 and another separation part 14 in the bag body 10 can also be matched to define a separate space S. In an embodiment, the separation parts 14 include a first separation part 14A and a second separation part 14B, the first separation part 14A and the second separation part 14B have the same shape and are arranged at an interval, and the first separation part 14A and the second separation part 14B respectively have different distances to the opening 13, but are not limited to this configuration. Thus, a first separate space S1 is defined between the first separation part 14A and the circumferential sealing part 12, a second separate space S2 is defined between the first separation part 14A and the second separation part 14B, and a third separate space S3 can be defined between the second separation part 14B and the circumferential sealing part 12. The first separate space S1, the second separate space S2 and the third separate space S3 respectively contain the reactant 22, the catalyst 23 and the reactive liquid 21, and a configuration of the reactive liquid 21, reactant 22 and catalyst 23 contained in the first separate space S1, second separate space S2 or third separate space S3 does not need to be restricted.

In this embodiment, the reactive liquid 21 can be water, but is not limited to this. The reactant 22 includes sodium percarbonate ($2Na_2CO_3 \cdot 3H_2O_2$); and the sodium percarbonate react with and can be decomposed to generate oxygen, wherein a chemical equation is $2Na_2CO_3 \cdot 3H_2O_2 \rightarrow 2Na_2CO_3 + 3H_2O + 3/2O_2$. The catalyst 23 is added and can increase an oxygen generation rate; and the catalyst 23 can be manganese sulfate ($MnSO_4$), enzyme or manganese dioxide ($MnO_2$).

In an embodiment, the separation part 14 is formed by hot sealing, and hot sealing force for forming the circumferential sealing part 12 and the separate sealing part 141 is greater than hot sealing force for forming the breakthrough part 142. Thereby, binding force between the circumferential sealing part 12 and the separate sealing part 141 is greater than binding force of the breakthrough part 142, i.e., the circumferential sealing part 12 and the separate sealing part 141 can endure larger force not to cause separation than the breakthrough part 142, thereby ensuring that the breakthrough part 142 can be separated prior to the circumferential sealing part 12 and the separate sealing part 141 when the user applies a force to the bag body 10, and ensuring that when the bag body 10 receives a force, part of the periphery 111 provided with the circumferential sealing part 12 can still be sealed while only the breakthrough part 142 is separated.

In an embodiment, in order to ensure the difference between the binding force of the breakthrough part 142 and the circumferential sealing part 12 and the binding force of the breakthrough part 142 and the separate sealing part 141, hot sealing area ranges of the foregoing structures can be changed; and setting of the required binding forces can also be ensured by enabling the hot sealing area range of the circumferential sealing part 12 and the separate sealing part 141 to be greater than the hot sealing area range of the breakthrough part 142.

Further referring to FIG. 2, the supporting components 30 are contained in the separate space S in which the oxygen-generating agent 20 reacts. In an embodiment, the supporting components 30 are contained in the first separate space S1. The supporting components 30 support the first separate space S1 so that the positions, corresponding to the first separate space S1 of the bag piece 10 cannot be completely compressed, i.e., the corresponding first separate space, containing the supporting components 30, of the bag piece 10 has a certain incompressible volume because of the arrangement of the supporting components 30, thereby ensuring that the oxygen-generating agent 20 cannot be extruded out of the first separate space S1 under compression.

In an embodiment, the volume of the separate space S containing the supporting components 30 is roughly equal to the volume of the reactive liquid 21, but is not limited to this, and the goal of generating oxygen in the bag body 10 of the present invention can be achieved on the basis that the total volume of the inner space of the bag body 10 is greater than the volume of the oxygen-generating agent 20. In other embodiments, there is still another feasible implementation manner that the volume of the separate space S containing the supporting components 30 is greater than the volume of the reactive liquid 21, so that the oxygen-generating agent 20 can be kept in the separate space S containing the supporting components 30 to react.

Also referring to FIG. 2, in an embodiment, the supporting components 30 is a hollow sphere with a penetration part 31. Thereby, the separate space S containing the supporting components 30 is supported by the supporting components 30, and thus can avoid extrusion to the oxygen-generating agent 20, which may cause the overflow of the oxygen-generating agent 20 via the opening 13, can be avoided when the separate space S is compressed. Besides, the supporting components 30 with the penetration part 31 can enable the oxygen-generating agent 20 to be thoroughly mixed without causing the obstruction to a reaction effect. It is worth noting that the form of the supporting components 30 is not limited to the foregoing embodiments. In other embodiments, a supporting components 30, which is a hollow body that is not spherical or is in other shapes or in the form of a bracket which stretches across and support two sides of the bag body 10 so that a part of the bag body 10 has a fixed and incompressible volume, is also a feasible implementation manner.

Still referring to FIG. 2, in an embodiment, the first separation part 14A is farther from the opening 13 than the second separation part 14B, a first separate space S1 is defined between the first separation part 14A and the circumferential sealing part 12, a second separate space S2 is defined between the first separation part 14A and the second separation part 14B, and a third separate space S3 is defined between the second separation part 14B and the circumferential sealing part 12. Hereby, the third separate space S3 is nearer to the opening 13 than the second separate space S2, and the second separate space S2 is nearer to the opening 13 than the first separate space S1. In addition, the first separate space S1 contains the reactant 22, the second separate space S2 contains the catalyst 23, and the third separate space S3 contains the reactive liquid 21.

When oxygen needs to be used, the user only needs to apply a force to the positions, corresponding to the separate spaces S, of the bag body 10, so that the breakthrough part 142 between every two separate spaces S is separated under pressure, and the reactive liquid 21, catalyst 23 and reactant 22 can be mixed in the communicating separate spaces S to perform an oxygen-generating reaction. In an embodiment, when the user uses the oxygen generator with the opening 13 facing up according to a using habit of most people, the reactive liquid 21 and the catalyst 23 can enter the first separate space S1 through the breakthrough parts 142 between every two separate spaces S and be mixed with the reactant 22 to perform the oxygen-generating reaction.

Further referring to FIG. 2, in an embodiment, the separate sealing part 141 of each separation part 14 is provided with a slope 1411, the slope 1411 is connected to the breakthrough part 142, and the slope 1411 facing the opening 13 is obliquely connected to the breakthrough part 142 in a direction far from the opening 13. Therefore, when the breakthrough part 142 is separated under pressure, the substance contained in each separate space S can move to the breakthrough part 142 under the guide of the slope 1411 so as to smoothly enter the separate space S far from the opening 13. Thereby, the catalyst 23 and the reactive liquid 21 contained in the second separate space S2 and the third separate space S3 can truly enter the first separate space S1 and react with the reactant 22, thereby ensuring that the oxygen-generating reaction can truly occur.

Figure 3:
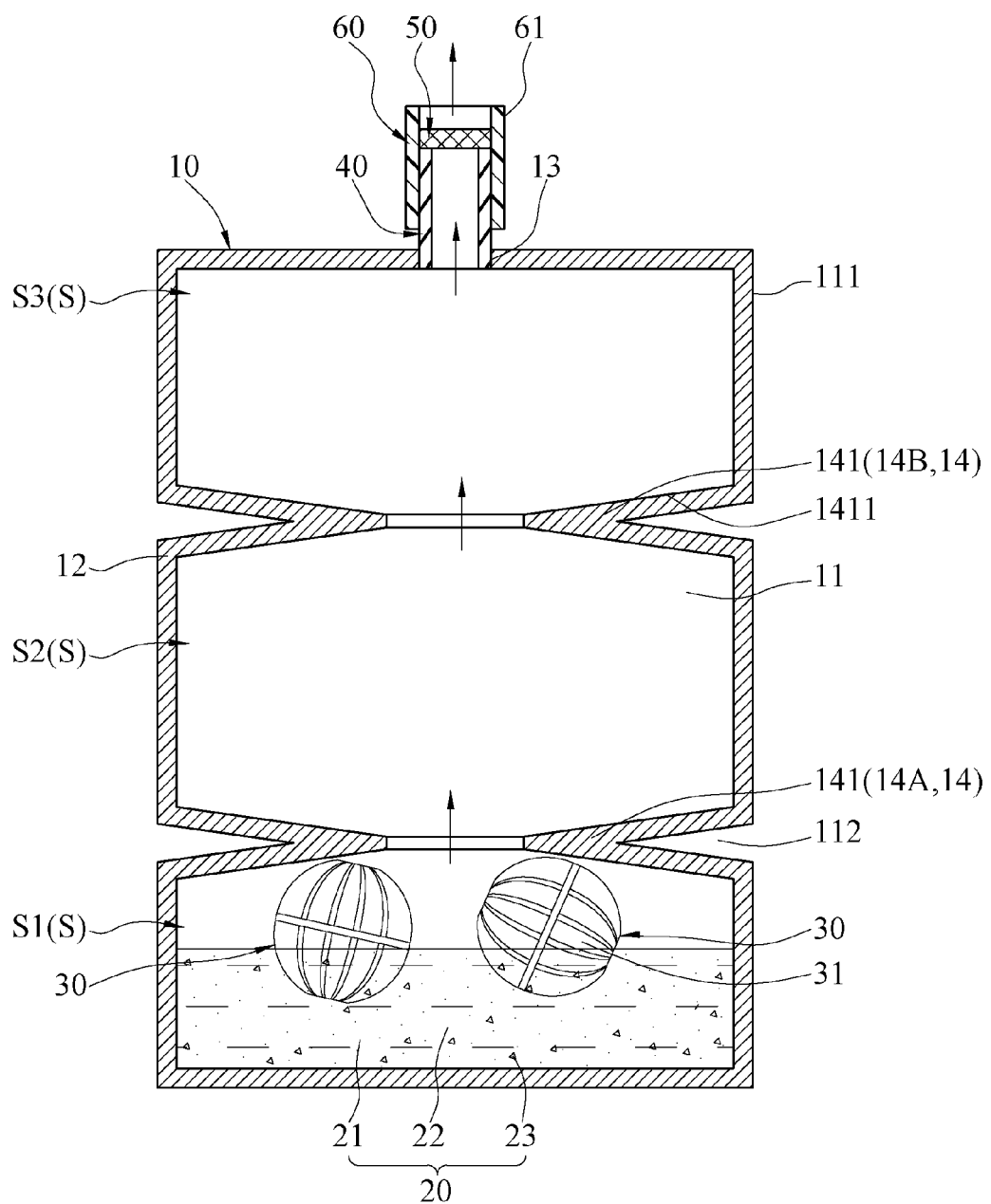
FIG. 3 is a section view of a use state of an embodiment of the oxygen generator of the present invention.

Referring to FIG. 3 in combination, in an embodiment, the supporting components 30 are made of a material of which the specific gravity is less than that of the reactive liquid 21, and thereby, the supporting components 30 are made of a plastic material. Therefore, after the reactive liquid 21 and the catalyst 23 enter the separate space S containing the reactant 22 through the breakthrough parts 142 between every two separate spaces S, the supporting components 30 can be suspended on the reactive liquid 21. Thus, when the oxygen-generating agent 20 is undergoing the oxygen-generating reaction, oxygen generated by the oxygen-generating reaction can disturb the reactive liquid 21, so that the supporting components 30 suspended on the reactive liquid 21 can rotate, jump or shift; and the supporting components 30 in the rotating, jumping or shifting process can also disturb the reactive liquid 21, so that the reactive liquid 21 is mixed with the reactant 22 and the catalyst 23 more thoroughly, thereby enhancing the reaction efficiency of the oxygen-generating agent 20. In an embodiment, the first separate space S contains the supporting components 30, and the volume of the first separate space S1 after containing the supporting components 30 is roughly equal to the volume of the oxygen-generating agent 20; thus, after the oxygen-generating agent 20 enters the first separate space S, the supporting components 30 are suspended on the topmost end of the first separate space S1, the supporting components 30 can abut against the first separation part 14A and be pushed by the buoyancy of the reactive liquid 21, and can disturb the reactive liquid 21 more thoroughly, so that the reactant 22 and the catalyst 23 can be mixed with the reactive liquid 21 more uniformly, thereby achieving an optimal oxygen-generating reaction effect.

It is worth noting that, in other embodiments, the volume of the second separate space S2 can be configured to be roughly equal to the volume of the catalyst 23, and the volume of the third separate space S3 is also configured to be roughly equal to the volume of the reactive liquid 21, so that a use ratio of the inner space of the bag body 10 is optimized, thereby lowering the overall volume and being more convenient to carry about.

Referring to FIG. 2 in combination, when the packing of the oxygen generator of the foregoing embodiment is finished, the reactive liquid 21, the reactant 22 and the catalyst 23 of the oxygen-generating agent 20 are respectively contained in different separate spaces S, and the soft bag body 10 can obviously reduce the volume, and thus, is more convenient for the user to carry. When oxygen needs to be used, referring to FIG. 3 in combination, as long as the bag body 10 is pressed to separate the separation parts 14 of the bag body 10, after the separation parts 14 are separated, the first separate space S1, the second separate space S2 and the third separate space S3 communicate, the reactive liquid 21 in the third separate space S3 and the catalyst 23 in the second separate space S2 can enter the first separate space S1 and be mixed with the reactant 22 to react so as to generate oxygen, and the oxygen generated by the oxygen-generating agent 20 can flow out of the opening 13 through the separation parts 14 and be used by the user.

Referring to FIG. 2 and FIG. 3, in an embodiment, the oxygen generator further includes a gas nozzle 40, the gas nozzle 40 is connected with the opening 13; and therefore, when the oxygen-generating agent 20 in the oxygen generator reacts to generate oxygen, the user can inhale the oxygen through the gas nozzle 40, thereby enhancing the use convenience.

Referring to FIG. 2 and FIG. 3, in an embodiment, the oxygen generator further includes a waterproof air-permeable film 50, and the waterproof air-permeable film 50 can be directly arranged on one end of the gas nozzle 40, so that the gas nozzle 40 can prevent the reactive liquid 21 in the oxygen generator from overflowing via the opening 13 in addition to being configured for the user to inhale oxygen, thereby generating a leakage prevention effect.

Referring to FIG. 2 and FIG. 3, in addition to being directly arranged on the gas nozzle 40, the waterproof air-permeable film 50, in an embodiment, can also be arranged between the two ends of an outer gas nozzle 60. Here, the outer gas nozzle 60 can be arranged on the gas nozzle 40 in a way of, but not limited to, sleeving, thereby facilitating the configuration or replacement of the waterproof air-permeable film 50; and the user can use oxygen directly through the outer gas nozzle 60. In addition, in this embodiment, a self-adhesive film 61 can be arranged on the other end of the outer gas nozzle 60, so that the waterproof air-permeable film 50 and the self-adhesive film 61 provide two leakage prevention mechanisms, thereby further ensuring that the overall oxygen generator cannot generate the condition of leakage of the reactive liquid 21. It is more worth noting that airtight seal is not required for sealing on the other end of the outer gas nozzle 60. In this embodiment, the self-adhesive film 61 is arranged on the outer gas nozzle 60 in a pasting mode; therefore, when the oxygen generator may be touched by accident and undergoes the oxygen-generating reaction unexpectedly, gas pressure of the oxygen generated in the bag body 10 is sufficient to cause the shedding of the self-adhesive film 61, and the oxygen generated in the bag body 10 can be discharged under such a condition, thereby lowering the gas pressure in the bag body 10; and thus, the condition of unexpected explosion due to exceed the gas pressure in the bag body 10 cannot occur, thereby enhancing the safety performance.

Figure 4:
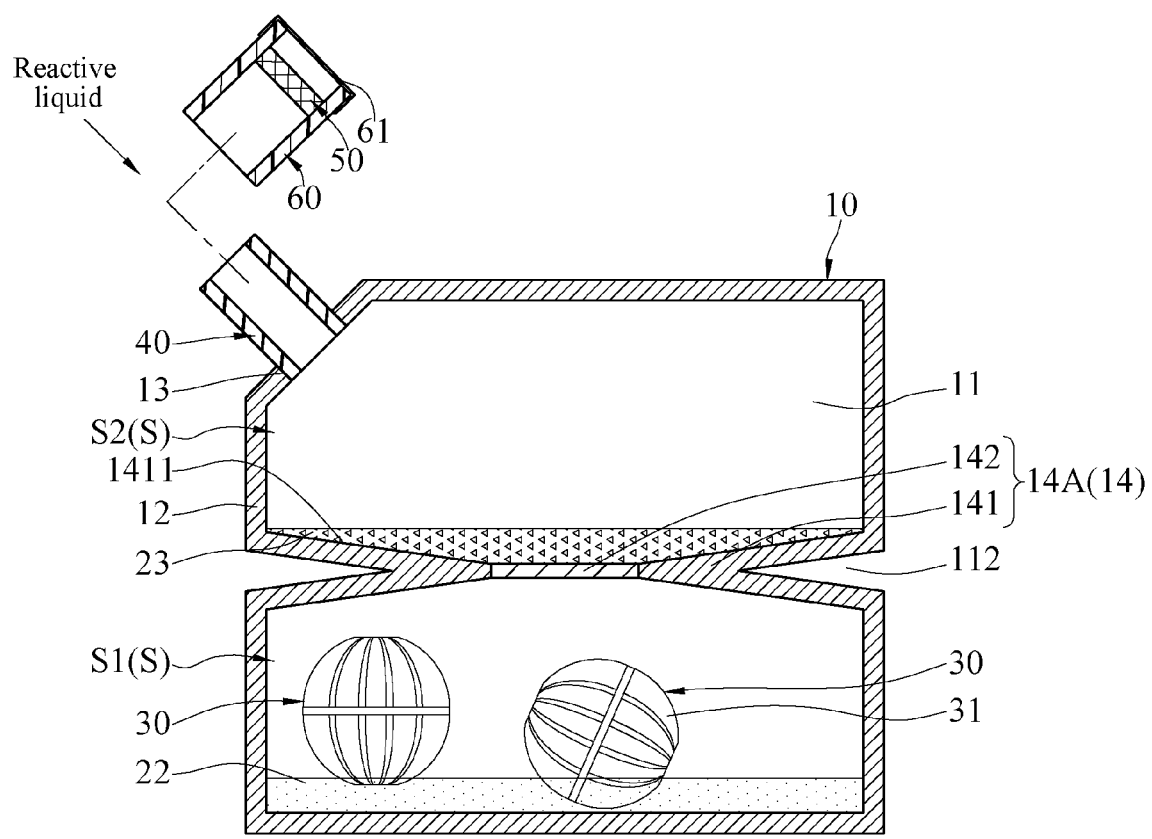
FIG. 4 is a section view of a local structure of another embodiment of the oxygen generator of the present invention.

Referring to FIG. 4 in combination, in an embodiment, in order to reduce the weight of the oxygen generator and further enhance the carry-on convenience, the bag body 10 can only contain the reactant 22 and the catalyst 23; and since water, which is an accessible substance, can also be used as reactive liquid 21, in this embodiment, the reactive liquid 21 can be added by the user himself/herself to react when the user needs to use oxygen. More specifically, in this embodiment, only the first separation part 14A is arranged in the bag body 10 to separate the bag body 10 into a first separate space S1 and a second separate space S2, and the first separate space S1 and the second separate space S2 respectively contain the reactant 22 and the catalyst 23. When oxygen needs to be used, the outer gas nozzle 60 is firstly removed to add the reactive liquid 21, so that the reactive liquid 21 in the second separate space S2 is firstly mixed with the catalyst 23, and then the outer gas nozzle 60 is put back and the bag body 10 is pressed, so that the first separation part 14A of the bag body 10 is separated; and after the first separation part 14A is separated, the reactive liquid 21 and the catalyst 23 which are mixed enter the first separate space S1 through the first separation part 14A, so that the reactive liquid 21 and the reactant 22 undergo the oxygen-generating reaction under the action of the catalyst 23. Here, the user can inhale oxygen through the outer gas nozzle 60 after ripping the self-adhesive film 61, and the reactive liquid 21 can be prevented from overflowing by the aid of the waterproof air-permeable film 50 in the outer gas nozzle 60. Thus, with such configuration, in addition of the reduction of the volume of the bag body 10 of the oxygen generator, the weight can also be reduced, so that the oxygen generator is more convenient to carry about and use.

Figure 5:
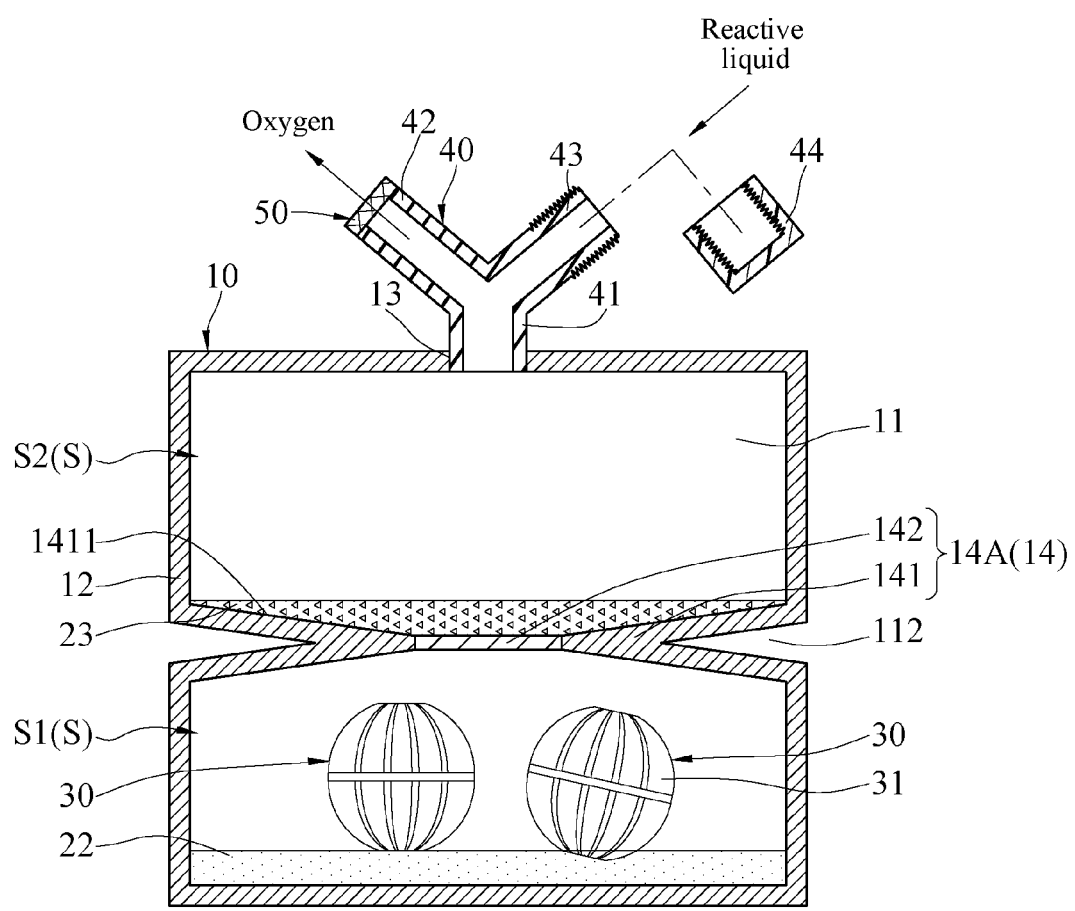
FIG. 5 is a section view of a local structure of still another embodiment of the oxygen generator of the present invention.

Referring to FIG. 5 in combination, in an embodiment, after further considering the convenience of adding the reactive liquid 21 by the user, in the oxygen generator into which the reactive liquid 21 must be added by the user himself/herself, the gas nozzle 40 is a three-way gas nozzle 40. Here, the gas nozzle 40 includes a first tube part 41, a second tube part 42 and a third tube part 43, the first tube part 41 is connected to the opening 13, the second tube part 42 is provided with the waterproof air-permeable film 50, and the third tube part 43 is matched with an outer cap 44. Thus, the user can add the reactive liquid 21 through the third tube part 43 and put the outer cap 44 back to the third tube part 43 after addition to prevent the reactive liquid 21 from leakage. The oxygen generated under the combined actions of the reactive liquid 21, the reactant 22 and the catalyst 23 can flow out for use via the second tube part 42. In this embodiment, since a position of adding the reactive liquid 21 is different from an oxygen discharge position, the third tube part 43 of the gas nozzle 40 can be configured to have a different shape from the second tube part 42; and the third tube part 43 is configured to be in a flared shape which facilitates the addition of the reactive liquid 21, and the second tube part 42 is configured to have the size and shape which are convenient for the user to inhale oxygen, thereby satisfying the convenience both in adding the reactive liquid 21 and in use. Further, in an embodiment, the outer cap 44 can be screwed with the third tube part 43 of the gas nozzle 40 through screw threads so as to enhance the convenience in disassembly and assembly.

Figure 6:
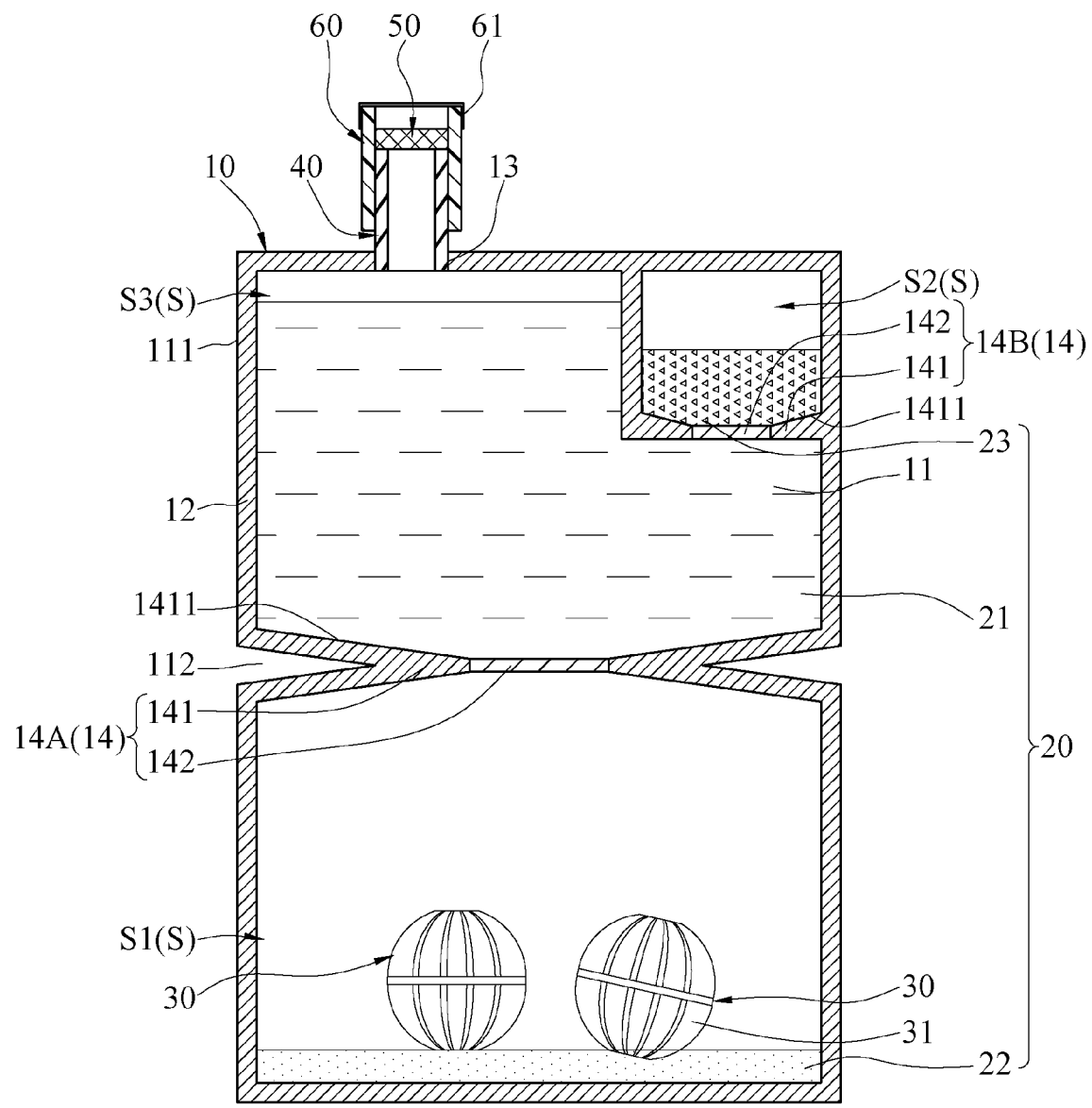
FIG. 6 is a section view of a local structure of still yet another embodiment of the oxygen generator of the present invention.

In an embodiment, please refer to FIG. 6 in combination for other configuration modes of the first separation part 14A and the second separation part 14B. Here, both ends of the first separation part 14A are connected to the circumferential sealing part 12 so as to separate the inner space of the bag body 10 into a first separate space S1 and a third separate space S3 which have different distances from the opening 13, the third separate space S3 being nearer to the opening 13 than the first separate space S1. The second separation part 14B is arranged in the third separate space S3, i.e., the second separation part 14B is nearer to the opening 13 than the first separation part 14A, and the second separation part 14B is in an L shape; and thereby, a second separate space S2 is defined between the second separation part 14B and the circumferential sealing part 12, and in a projection direction perpendicular to the bag piece 10, the area of the second separate space S2 is less than one half of the area of the first separate space S1, and is also less than one half of the area of the third separate space S3.

In this embodiment, the first separate space S1 contains the reactant 22, the second separate space S2 contains the catalyst 23, and the third separate space S3 contains the reactive liquid 21. According to this configuration, the catalyst 23 is contained in a corner of the top of the bag body 10, and the area of the second separate space S2 containing the catalyst 23 is reduced.

Thus, when the user uses the oxygen generator, the bag body 10 contains the reactive liquid 21 in a liquid state and is provided with the opening 13 for gas discharge, so in this situation, the user will normally consider the side, with the opening 13, of the bag body 10 as an upper side and a position corresponding to the first separate space S1 as a lower side. Thus, according to the using habit of most people, most users will extrude the bag body 10 from the upper side to the lower side, i.e., according to the common using habits, the user will firstly press the second separate space S2 on the upper side and then press the third separate space S3 or first separate space S1 on the lower side of the second separate space S2.

Therefore, when the user applies a force firstly to the second separate space S2, the breakthrough part 142 of the second separation part 14B will be separated firstly, so that the catalyst 23 firstly enters the third separate space S3 and is mixed with the reactive liquid 21, and the reactive liquid 21 in the liquid state can be thoroughly mixed with the catalyst 23. Then, a force is applied to the first separate space S1 or third separate space S3 so that the first separation part 14A is separated, at this time, the catalyst 23 thoroughly mixed with the reactive liquid 21 can reenter the first separate space S1 to act with the reactant 22; and according to this sequence of operation, the catalyst 23 can react with the reactant 22 after previously contacting and being uniformly mixed with the reactive liquid 21, thereby enhancing the oxygen generation stability.

On such a basis, from the aspect of use safety, when the second separate space S2 is configured to be in the topmost position of the bag body 10, according to the description above, the user firstly applies a force to the second separate space S2 and then applies a force to the first separate space S1 or third separate space S3 according to the conventional using habit, so that the catalyst 23 is firstly mixed with the reactive liquid 21 in the third separate space S3 to lower the concentration of the catalyst 23 and then is mixed with the reactant 22, thereby preventing the reactant 22 from directly reacting with the undiluted catalyst 23, further reducing the oxygen-generating speed, avoiding the occurrence of instantaneous violent reaction, and thus, enhancing the use safety.

In addition, when the oxygen generator is stored and not in use, even if the bag body 10 of the oxygen generator is stressed due to touch by accident, based on the configuration of the embodiment as shown in FIG. 6, the catalyst 23 cannot directly contact the reactant 22 separately no matter the first separation part 14A or the second separation part 14B is firstly separated, thereby ensuring the storage safety of the oxygen generator and giving consideration to safety problems in both use and storage.

Certainly, in order to further ensure the user to use the oxygen generator in a preferable use sequence so that the oxygen generator can perform stable and safe oxygen-generating reaction, marking patterns can be arranged in positions, corresponding to the separate spaces S, outside the bag body 10 so as to indicate the use sequence to the user, for example, a position, corresponding to the second separate space S2, outside the bag body 10 is marked as "1", and a position corresponding to the third separate space S3 is marked as "2"; and in this way, the user can receive the indication more directly and use the oxygen generator in the preferable use sequence.

Figure 7:
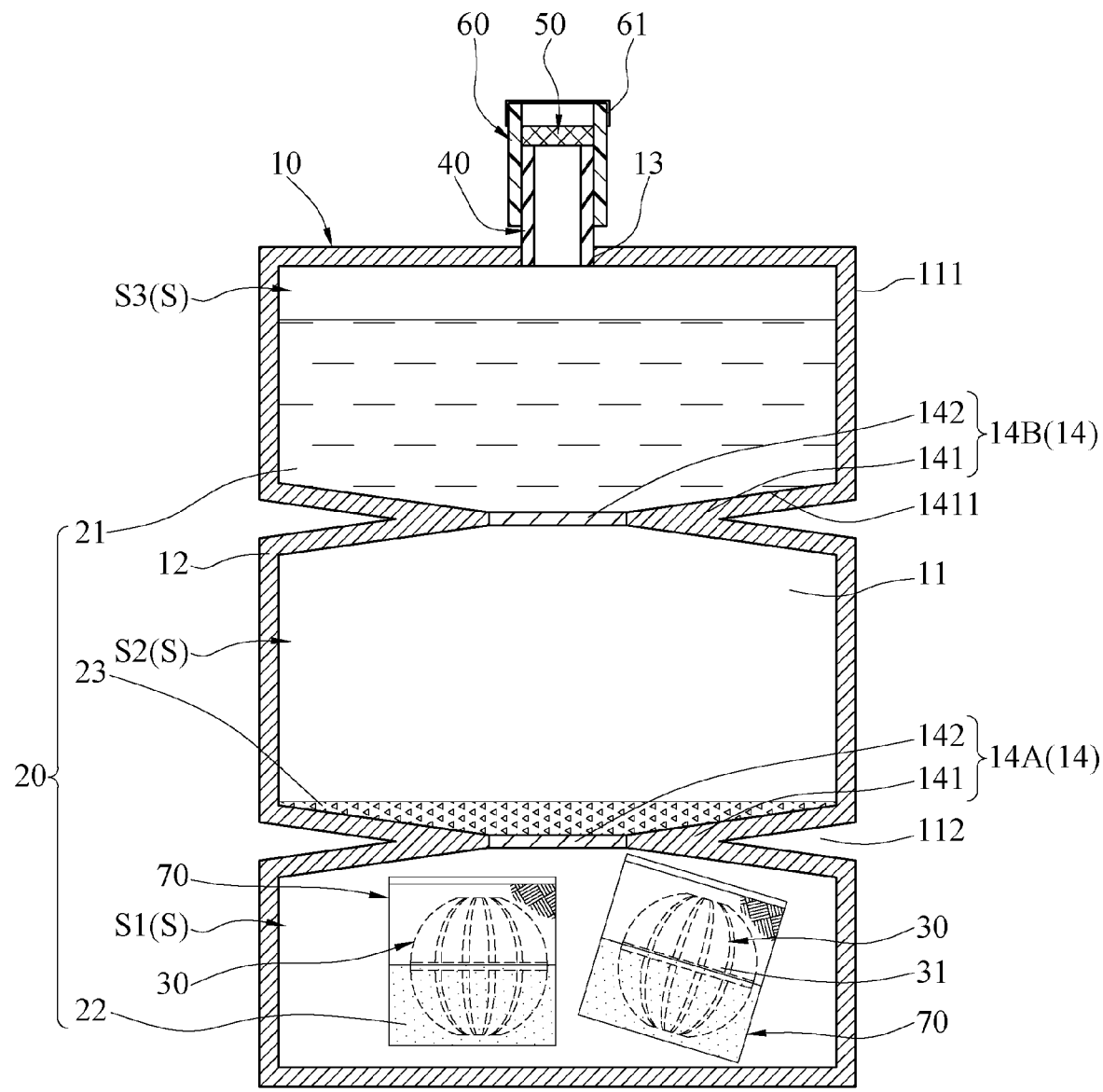
FIG. 7 is a schematic diagram of an additional mesh bag of an embodiment of the oxygen generator of the present invention.

Also referring to FIG. 6, in an embodiment, the liquid level of the reactive liquid 21 contained in the third separate space S3 is higher than the height of the catalyst 23 in the second separate space S2, i.e., the liquid level of the reactive liquid 21 in the third separate space S3 is nearer to the opening 13 than the catalyst 23. Thus, when the breakthrough part 142 of the second separation part 14B is separated, the second separate space S2 communicates with the third separate space S3, so the reactive liquid 21 in the third separate space S3 will enter the second separate space S2; and the reactive liquid 21 in the liquid state can take all the catalyst 23 in the liquid state out of the second separate space S2 so as to lower the quantity of the catalyst 23 remaining in the second separate space S2 as much as possible, so that the catalyst 23 can be used thoroughly, thereby ensuring the stable proceeding of the oxygen-generating reaction. Referring to FIG. 7 in combination, in an embodiment, the oxygen generator further includes a mesh bag 70, the mesh bag 70 is a bag-like body made of a porous material, the reactant 22 and the supporting components 30 are contained in the mesh bag 70, and the mesh bag 70 is contained in the first separate space S1. Thereby, after the user operates to enable the separate spaces S to communicate, the reactive liquid 21 and the catalyst 23 cannot immediately and directly contact the reactant 22, and the mesh bag 70 is used as a buffer of the reaction, thereby lowering the oxygen-generating speed. Therefore, the added mesh bag 70 can reduce the speed of the oxygen-generating reaction, and the effect of adjusting the oxygen-generating speed can be further achieved by changing the pore size or density of the mesh bag 70, thereby providing a required oxygen-generating speed to satisfy different use demands.

Figure 8:
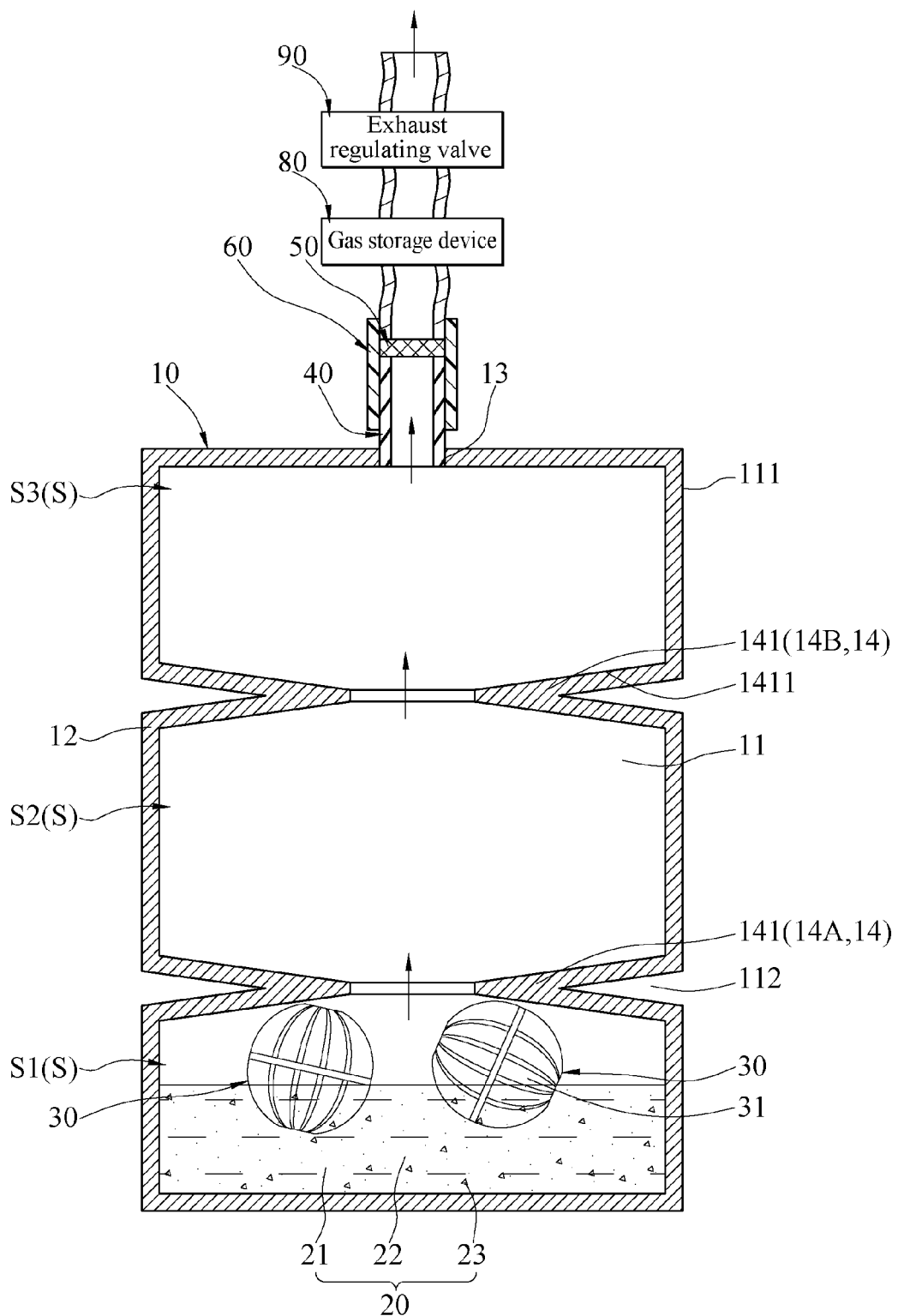
FIG. 8 is a schematic diagram of an additional gas storage device and exhaust regulating valve of an embodiment of the oxygen generator of the present invention.

Referring to FIG. 8 in combination, in an embodiment, the oxygen generator can further include a gas storage device 80 and an exhaust regulating valve 90, the gas storage device 80 being connected with the opening 13; and if the opening 13 is in the implementation manner being connected with the gas nozzle 40 or the outer gas nozzle 60, the gas storage device 80 may also be connected with the gas nozzle 40 or the outer gas nozzle 60. The exhaust regulating valve 90 is connected with the gas storage device 80. Herein, the oxygen-generating agent 20 will react persistently to the end once starting a reaction for one time, and the quantity of the oxygen generated by the reaction of the oxygen-generating agent 20 for one time cannot be used up for one time; and therefore, in this embodiment, when the oxygen-generating agent 20 reacts, the oxygen generated by the oxygen-generating agent 20 can be firstly stored in the gas storage device 80, and the user exhausts the oxygen for use through the exhaust regulating valve 90 according to needs. Thus, the quantity of the oxygen generated by the reaction of the oxygen-generating agent 20 for one time can be thoroughly used, thereby reducing unnecessary waste. In an embodiment, the gas storage device 80 may be a soft and elastic rubber container, and thus, the required occupied space can be lowered when the gas storage quantity is lower; and if an explosion occurs due to exceed gas storage quantity, it cannot cause safety hazards to people around, thereby ensuring the safety of stored gas.

Further referring to FIG. 2, FIG. 4 and FIG. 6, in an embodiment, the position of the bag piece 11, corresponding to the separation part 14, of the bag body 10 can also be provided with a notch 112, i.e., the notch 112 can be positioned between the first separate space S1 and the second separate space S2, and can also be positioned between the second separate space S2 and the third separate space S3. Here, the notches 112 provide spaces for the movement of the bag piece 11 relative to the adjacent separate spaces S. Thus, when the separate spaces S are sealed, no matter the circumferential sealing part 12 or the separation part 14 is hot sealing to be formed, hot sealing forming pressure can be converted into power for moving or compressing the bag piece 11, thereby preventing the rest hot sealing parts from being separated due to intensive stress, lowering the probability of forming failure or damage, and enhancing the product yield.

In conclusion, in the present invention, all the substances of the oxygen-generating agent 20 are separately packed in the different separate spaces S of the soft bag body 10, and a pressure is applied to the bag body 10 to enable the separate spaces S in the bag body 10 to communicate, so that the substances of the oxygen-generating agent 20 are mixed and react to generate oxygen. Compared with an oxygen generator with the oxygen-generating agent 20 contained in incompressible containers, the oxygen generator of the present invention can obviously reduce the volume occupation, is very convenient to use, and is more convenient to carry about.

Although the present invention has been described in considerable detail with reference to certain preferred embodiments thereof, the disclosure is not for limiting the scope of the invention. Persons having ordinary skill in the art may make various modifications and changes without departing from the scope and spirit of the invention. Therefore, the scope of the appended claims should not be limited to the description of the preferred embodiments described above.

What is claimed is:

1. An oxygen generator, comprising:
a bag body containing an oxygen-generating agent, wherein the oxygen-generating agent comprises reactive liquid, a reactant and a catalyst, and the bag body comprises:
a bag piece, provided with a periphery;
a circumferential sealing part, arranged on a part of the periphery of the bag piece and bound with the periphery of the bag piece, wherein the circumferential sealing part enables the binding of part of the periphery so as to define a range of an inner space, and a range of the rest part of the periphery of the bag piece defines an opening; and
a separation part, provided with a breakthrough part, wherein both ends of the separation part are connected to the circumferential sealing part so that the inner space is separated into a plurality of separate spaces, and the plurality of separate spaces respectively contain the reactant and the catalyst; and
a supporting component, contained in one of the plurality of separate spaces, wherein the position, corresponding to the supporting component, of the bag body is incompressible, wherein the supporting component is a hollow sphere and is provided with a plurality of penetration parts.

2. The oxygen generator of claim 1, wherein the specific gravity of the supporting component is less than the specific gravity of the reactive liquid.

3. The oxygen generator of claim 1, wherein the bag body comprises a plurality of separation parts, each of the plurality of separation parts comprises a first separation part and a second separation part, a first separate space is defined between the first separation part and the circumferential sealing part, a second separate space is defined between the second separation part and the first separation part, and a third separate space is defined between the second separation part and the circumferential sealing part.

4. The oxygen generator of claim 3, wherein in a direction perpendicular to the first separation part, the third separate space is nearer to the opening than the second separate space.

5. The oxygen generator of claim 4, wherein the first separate space contains the reactant, the second separate space contains the catalyst, and the third separate space contains the reactive liquid.

6. The oxygen generator of claim 1, wherein the bag body comprises a plurality of separation parts, each of the plurality of separation parts comprises a first separation part and a second separation part, a first separate space is defined between the first separation part and the circumferential sealing part, a second separate space is defined between the second separation part and the circumferential sealing part, and a third separate space is defined between the second separation part and the first separation part.

7. The oxygen generator of claim 6, wherein in a direction perpendicular to the first separation part, the position of the second separate space is nearer to the opening than the position of the third separate space.

8. The oxygen generator of claim 7, wherein the first separate space contains the reactant, the second separate space contains the catalyst, and the third separate space contains the reactive liquid.

9. The oxygen generator of claim 1, further comprising a gas storage device and an exhaust regulating valve, wherein the gas storage device is connected with the opening, and the exhaust regulating valve is connected to the gas storage device.

10. The oxygen generator of claim 1, wherein the bag body comprises a plurality of separation parts, each of the plurality of separation parts is further provided with a slope, the slope is connected to the breakthrough part, and the slope facing the opening is obliquely connected to the breakthrough part in a direction remote from the opening.

11. The oxygen generator of claim 1, wherein the bag piece is further provided with a notch, and the position of the notch corresponds to the position of the separation part.

12. The oxygen generator of claim 1, further comprising a gas nozzle, wherein the gas nozzle is connected to the opening.

13. The oxygen generator of claim 12, further comprising an outer gas nozzle, wherein one end of the outer gas nozzle is arranged on the gas nozzle, and a waterproof air-permeable film is arranged between two ends.

14. The oxygen generator of claim 13, wherein the other end of the outer gas nozzle is provided with a self-adhesive film.

15. The oxygen generator of claim 1, wherein the separation part further comprises a separate sealing part, the separate sealing part is of an inseparable binding structure, and the breakthrough part is a separable binding structure.

16. The oxygen generator of claim 15, wherein the breakthrough part is a zipper lock or is formed by hot sealing.

17. An oxygen generator, comprising:
 a bag body containing an oxygen-generating agent, wherein the oxygen-generating agent comprises reactive liquid, a reactant and a catalyst, and the bag body comprises:
  a bag piece, provided with a periphery;
  a circumferential sealing part, arranged on a part of the periphery of the bag piece and bound with the periphery of the bag piece, wherein the circumferential sealing part enables the binding of part of the periphery so as to define a range of an inner space, and a range of the rest part of the periphery of the bag piece defines an opening; and
  a separation part, provided with a breakthrough part, wherein both ends of the separation part are connected to the circumferential sealing part so that the inner space is separated into a plurality of separate spaces, and the plurality of separate spaces respectively contain the reactant and the catalyst; and
 a supporting component, contained in one of the plurality of separate spaces, wherein the position, corresponding to the supporting component, of the bag body is incompressible; and
 a mesh bag, wherein the reactant is contained in the mesh bag, and the mesh bag covers the supporting component.

* * * * *